United States Patent
Huang et al.

(10) Patent No.: US 9,751,845 B2
(45) Date of Patent: Sep. 5, 2017

(54) 5-HT2B ANTAGONISTS

(71) Applicant: National Institute of Biological Sciences, Beijing, Beijing (CN)

(72) Inventors: Niu Huang, Beijing (CN); Yu Zhou, Beijing (CN); Xingyu Lin, Beijing (CN)

(73) Assignee: National Institute of Biological Sciences, Beijing, Beijing (CN)

( * ) Notice: Subject to any disclaimer, the term of this patent is extended or adjusted under 35 U.S.C. 154(b) by 0 days.

(21) Appl. No.: 15/292,143

(22) Filed: Oct. 13, 2016

(65) Prior Publication Data

US 2017/0029385 A1    Feb. 2, 2017

Related U.S. Application Data

(63) Continuation of application No. PCT/CN2015/076079, filed on Apr. 8, 2015, which is a continuation of application No. PCT/CN2014/075285, filed on Apr. 14, 2014.

(51) Int. Cl.
| | |
|---|---|
| *A61K 31/53* | (2006.01) |
| *C07D 251/72* | (2006.01) |
| *A61K 45/06* | (2006.01) |
| *C07D 251/10* | (2006.01) |

(52) U.S. Cl.
CPC ............ *C07D 251/72* (2013.01); *A61K 31/53* (2013.01); *A61K 45/06* (2013.01); *C07D 251/10* (2013.01)

(58) Field of Classification Search
CPC ..................................................... A61K 31/53
USPC ........................................................ 514/245
See application file for complete search history.

(56) References Cited

FOREIGN PATENT DOCUMENTS

| WO | WO2009051801 A2 | 4/2009 |
|---|---|---|
| WO | WO2012149266 A1 | 11/2012 |

OTHER PUBLICATIONS

Database PubChem Compound, XP002766286, NCBI Database accession No. 3649661, Sep. 9, 2005.
Extended European Search Report of counterpart EP No. 15779947.9.

*Primary Examiner* — Kevin E Weddington
(74) *Attorney, Agent, or Firm* — Richard Aron Osman

(57) ABSTRACT

The invention provides novel compounds and compositions comprising a 5-$HT_{2B}$ antagonist of formula I:

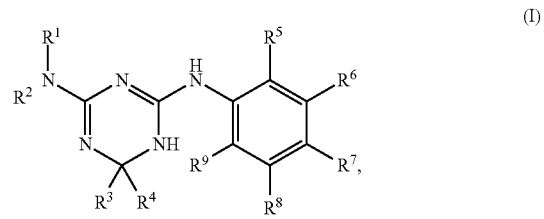

and related methods for treating a person having a disorder characterized by undesirable 5-$HT_{2B}$ receptor signaling, such as migraine, irritable bowel syndrome (IBS), pulmonary arterial hypertension (PAH), fibrosis, hepatocellular cancer, a small intestinal neuroendocrine tumor, cardiovascular disorders, and gastrointestinal (GI) tract disorders.

20 Claims, No Drawings

5-HT2B ANTAGONISTS

This application is a continuation of PCT/CN2015/076079; Filed: Apr. 8, 2015, which claims priority to PCT/CN2014/075285; Filed: Apr. 14, 2014.

INTRODUCTION

G-protein coupled receptors (GPCRs) are involved in numerous physiological processes and represent major pharmaceutical targets in drug discovery. Over 40% of marketed drugs act through modulating GPCRs.[1] In the past, GPCR drugs were mainly discovered based on traditional medicinal chemistry approach, which restricted GPCR drugs to limited scaffold space. More recently, docking screens against GPCR crystal structures have been successfully applied in identification of new potent ligands.[2-4]

One recently determined GPCR structures is $5\text{-HT}_{2B}$ receptor.[5,6] It belongs to $5\text{-HT}_2$ receptor family, which is comprised of three subtypes: $5\text{-HT}_{2A}$, $5\text{-HT}_{2B}$ and $5\text{-HT}_{2C}$. Although both $5\text{-HT}_{2A}$ and $5\text{-HT}_{2C}$ receptors have been widely studied as therapeutic targets, research on $5\text{-HT}_{2B}$ has been limited. $5\text{-HT}_{2B}$ agonism has been regarded as an off-target since it activation is related to cardiac hypertrophy and pulmonary hypertension.[7,8] Many recent studies have focused on the possible application of $5\text{-HT}_{2B}$ antagonists.[9] Several compounds have advanced to clinical trials or pre-clinical research as treatments for migraine disorders,[10] irritable bowel syndrome (IBS),[11,12] pulmonary arterial hypertension (PAH)[13,14] and fibrosis.[15] Besides, some studies have suggested that 5-HT could promote cell survival and growth of hepatocellular carcinoma (HCC) by activation of $5\text{-HT}_{2B}$ receptor.[16,17] And our recent research has discovered that sorafenib, a kinase drug approved to treat hepatocellular carcinoma, also binds to $5\text{-HT}_{2B}$ receptor, which indicated that the binding of $5\text{-HT}_{2B}$ receptor might contribute to the sorafenib-produced anticancer effect.[18] Currently, only few highly selective $5\text{-HT}_{2B}$ antagonists have been reported due to high degree of homology with its close members, which hamper the further understanding of the $5\text{-HT}_{2B}$ receptor roles.[19] Therefore, discovery of novel and selective $5\text{-HT}_{2B}$ antagonist would be of great interest to further explore the function and therapeutic application of $5\text{-HT}_{2B}$ receptor.

Ma et al. (Bioorg. Med. Chem. Lett. 19, 2009, 5644-7) disclose 2,4-diamino-1,3,5-triazine derivatives, including related compounds 5a-5j, that "could be used as leads for the discovery of neuronal sodium channels blockers for managing central nervous system related disorders" (abstract) and provides "a lead molecule for further investigation and optimization for neuronal sodium channel binding activity, the therapeutic benefits of which are yet to be established" (final sentence).

US 2009/0226422A1 discloses Table 3, a list of hundreds of compounds including related compounds 82 and 320 (N-4-(4-methoxyphenyl)-1,3,5-triazaspiro[5.5]undeca-1,3-diene-2,4-diamine and N-4-(3-methoxyphenyl)-1,3,5-triazaspiro[5.5]undeca-1,3-diene-2,4-diamine), "identified by E47-ID1 interaction mapping as potentially inhibiting E47-Id1 interaction", wherein Id1 is an inhibitor of differentiation protein, and E47 is a ubiquitously expressed transcription factor which can bind and be sequestered by Id1. US 2009/0226422A1 teaches nothing further about these two compounds, other than they might potentially inhibit E47-Id1 interaction, and these compounds are not encompassed by the compounds alleged to be useful for treating proliferative disorders, i.e. formulas I-IV.

WO2010024225 and WO2012149266 also disclose related compounds.

SUMMARY OF THE INVENTION

The invention provides methods and compositions for treating a person having a disorder characterized by over-, or undesirable $5\text{-HT}_{2B}$ receptor signaling, comprising administering to the person a $5\text{-HT}_{2B}$ antagonist of formula I:

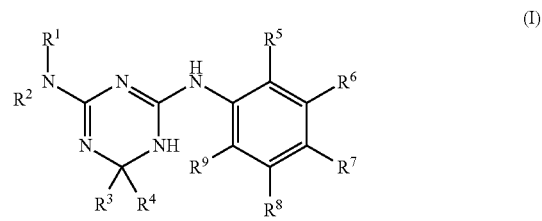

(I)

wherein:

$R^1$ and $R^2$ are independently H or methyl;

$R^3$ and $R^4$ are independently a C1-C4 alkyl, or $R^3$ and $R^4$ are joined to form a C3-C8 cycloalkyl; and $R^5$-$R^9$ are independently H or an optionally substituted heteroatom (particularly halogen or hydroxyl), or C1-C4 alkyl, C1-C4 alkyloxy, carbonyl, carboxyl, or amine, each of which is optionally substituted and may optionally comprise 1-3 heteroatoms; or salt thereof.

In embodiments:

$R^1$ and $R^2$ are independently H or methyl;

$R^3$ and $R^4$ are independently C1-C3 alkyl, or $R^3$ and $R^4$ are joined to form C4-C7 cycloalkyl;

$R^5$ and $R^9$ are independently H, halogen, methyl or methoxyl; and/or $R^6$-$R^8$ are independently H, halogen, methyl, $-OR^{10}$, $COR^{10}$, $COOR^{10}$, or $CONR^{10}R^{10}$, wherein each $R^{10}$ is independently H or C1-C4 alkyl.

In further embodiments:

$R^1$ and $R^2$ are independently H or methyl;

$R^3$ and $R^4$ are methyl or $R^3$ and $R^4$ form cyclopentyl or cyclohexyl;

$R^5$ is H, halogen, methyl or methoxyl;

$R^6$ is H, halogen (F, Cl, Br, I), methyl, methoxyl, or $-OR^{10}$, $COR^{10}$, $COOR^{10}$, or $CONR^{10}R^{10}$, wherein each $R^{10}$ is independently H or C1-C4 alkyl.

$R^7$ is H, halogen, methyl, $-OR^{10}$ or $COOR^{10}$, wherein each $R^{10}$ is independently H or C1-C3 alkyl;

$R^8$ is H, halogen, methyl or methoxyl; and/or $R^9$ is H or methyl.

In further embodiments the antagonist is of formula:

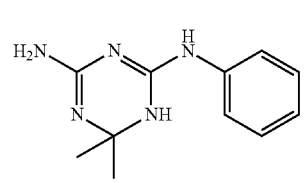 [SMILES: CC1(C)N=C(N)N=C(Nc2ccccc2)N1]

1-a

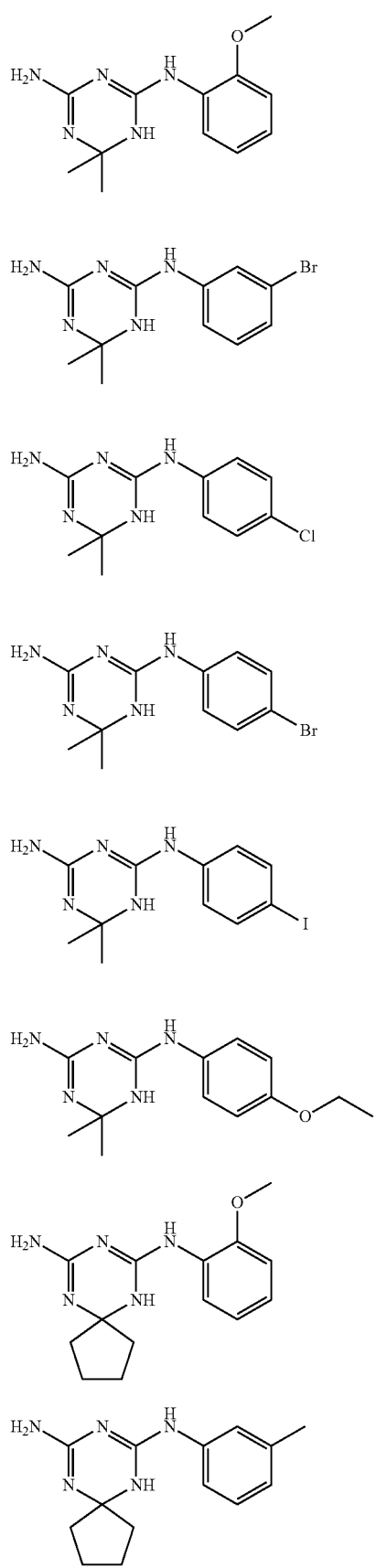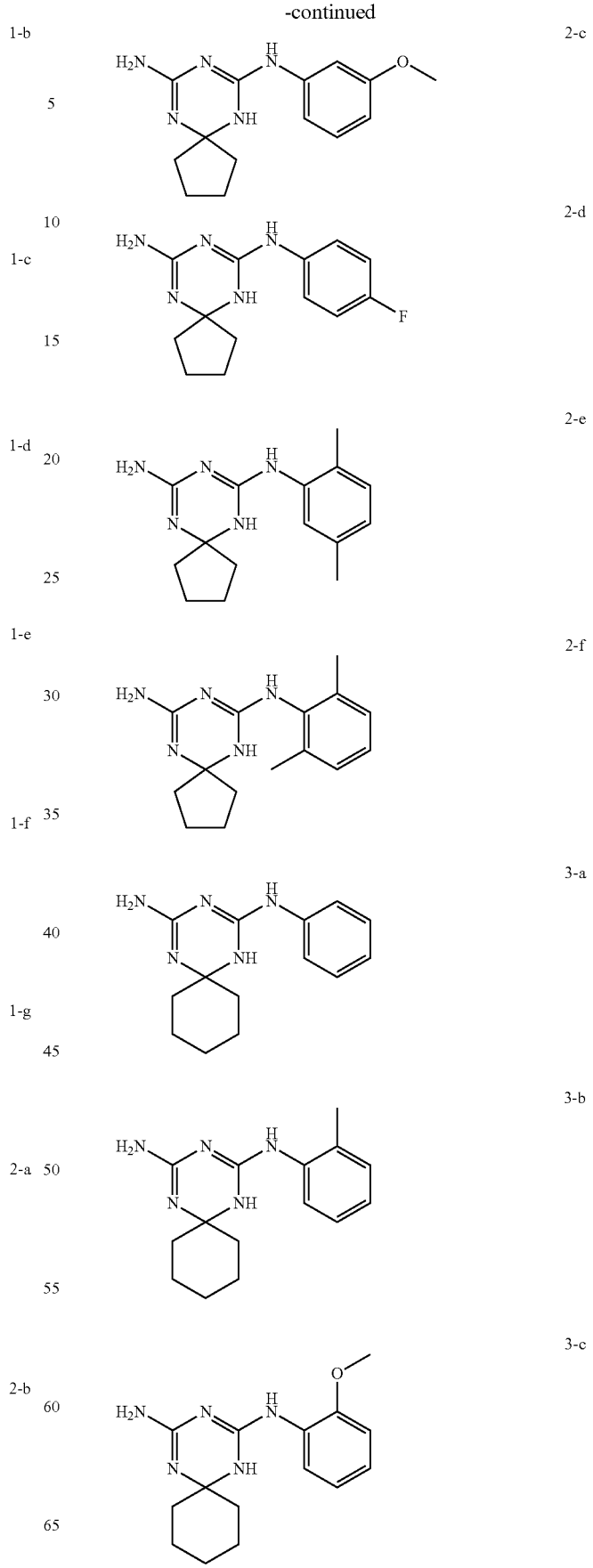

3-d
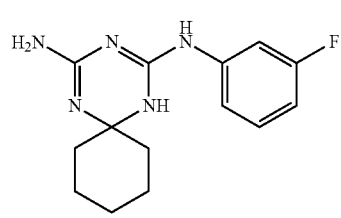 [SMILES: NC1=NC2(CCCCC2)NC(Nc2cccc(F)c2)=N1]
3-e1
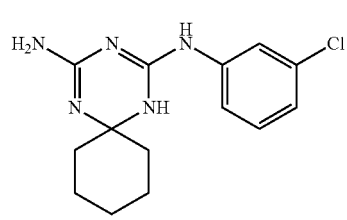 [SMILES: NC1=NC2(CCCCC2)NC(Nc2cccc(Br)c2)=N1]
3-e2
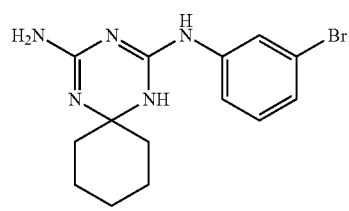
3-f
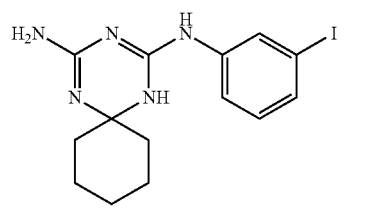 [SMILES: NC1=NC2(CCCCC2)NC(Nc2cccc(I)c2)=N1]
3-g
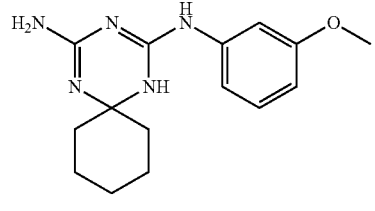 [SMILES: COc1cccc(NC2=NC(N)=NC3(CCCCC3)N2)c1]
3-h
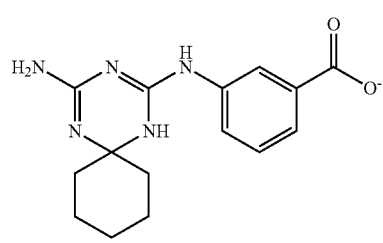 [SMILES: NC1=NC2(CCCCC2)NC(Nc2cccc(C(=O)[O-])c2)=N1]
3-i
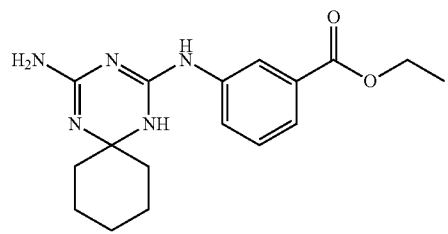
3-j
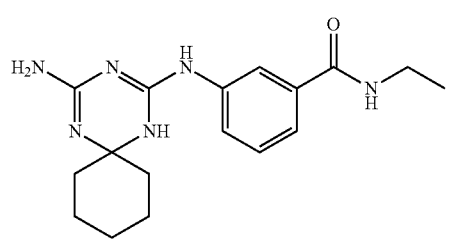
3-k
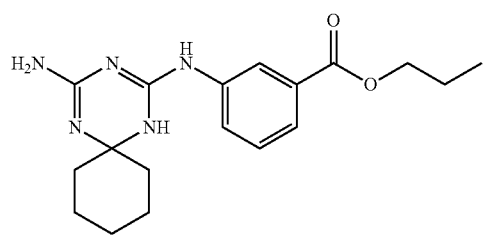
3-l
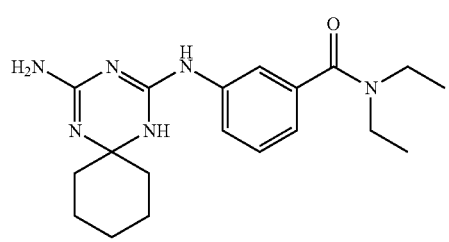
3-m
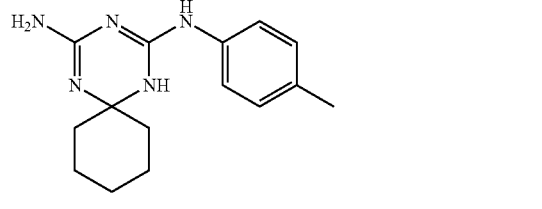
3-n
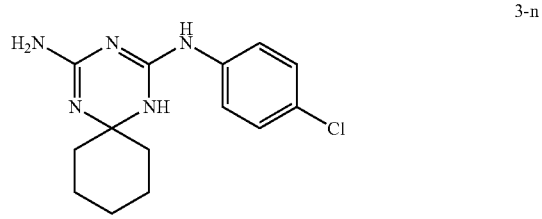
3-o
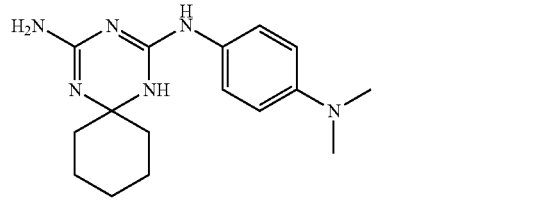
3-p
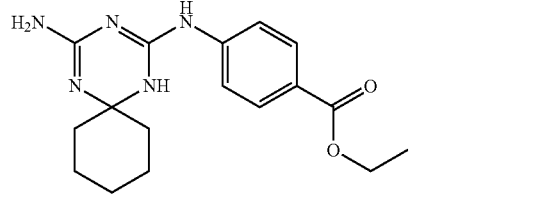

3-q 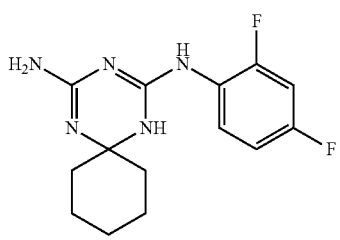

3-r 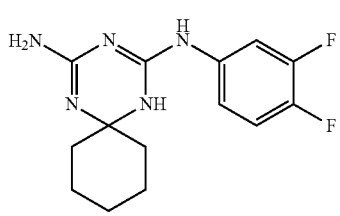

3-s 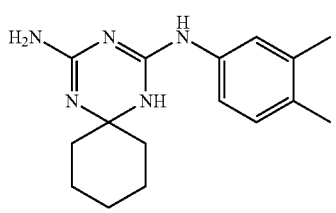

3-t 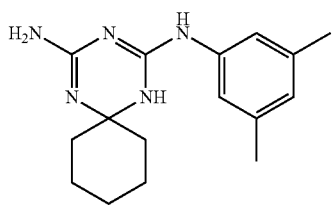

3-u 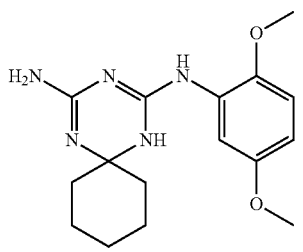

3-v 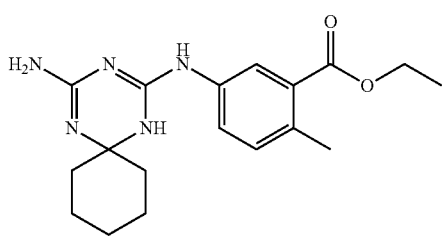

3-w 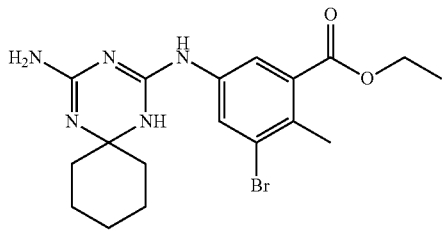

3-x 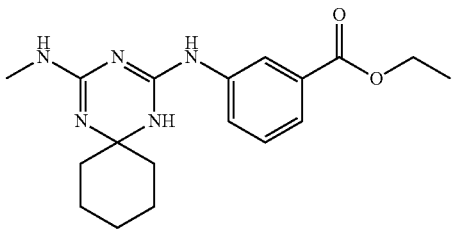

3-y 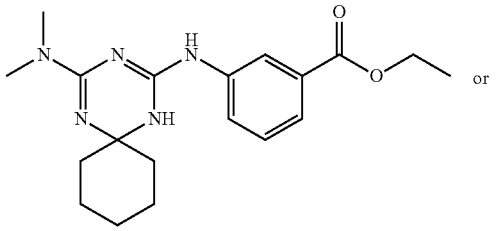 or 3-z 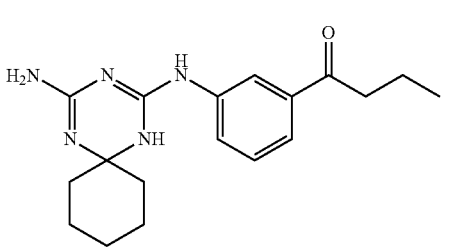

In embodiments, the disorder is migraine, irritable bowel syndrome (IBS), pulmonary arterial hypertension (PAH), fibrosis, hepatocellular cancer, a small intestinal neuroendocrine tumor, a cardiovascular disorder, or a gastrointestinal (GI) tract disorder.

In embodiments, the method further comprises the subsequent step of detecting a resultant amelioration of the disorder, and/or the antecedent step of diagnosing the disorder, particularly wherein the disorder is migraine, irritable bowel syndrome (IBS), pulmonary arterial hypertension (PAH), fibrosis, hepatocellular cancer, a small intestinal neuroendocrine tumor, a cardiovascular disorder, or a gastrointestinal (GI) tract disorder.

The invention also provides pharmaceutical compositions comprising a subject 5-HT$_{2B}$ antagonist and a second, different drug indicted for a disorder characterized by over-, or undesirable 5-HT$_{2B}$ receptor signaling, particularly migraine, irritable bowel syndrome (IBS), pulmonary arterial hypertension (PAH), fibrosis, hepatocellular cancer, a small intestinal neuroendocrine tumor, a cardiovascular disorder, or a gastrointestinal (GI) tract disorder.

The invention also provides novel compounds, compositions are related methods, wherein the compound is a 5-HT$_{2B}$ antagonist of formula I:

(I)
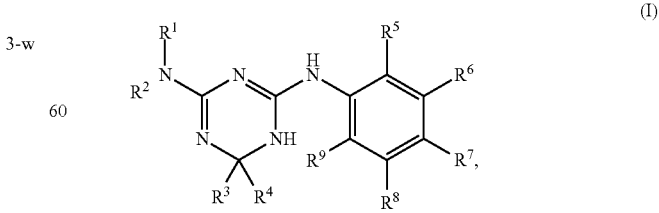

wherein:
$R^1$ and $R^2$ are independently H or Me;
$R^3$ and $R^4$ form cyclohexyl;

$R^5$ is H;
$R^6$ is $COR^{10}$, $COOR^{10}$, or $CONR^{10}R^{10}$, wherein each $R^{10}$ is independently H or C1-C3 alkyl;
$R^7$ is H or methyl;
$R^8$ is H or halogen; and
$R^9$ is H; or salt thereof.

In embodiments,
(3-e1) $R^1$=H, $R^2$=H, $R^6$ is Cl, $R^7$=H, $R^8$=H;
(3-e2) $R^1$=H, $R^2$=H, $R^6$ is Br, $R^7$=H, $R^8$=H;
(3-f) $R^1$=H, $R^2$=H, $R^6$ is I, $R^7$=H, $R^8$=H;
(3-j) $R^1$=H, $R^2$=H, $R^6$ is CONHEt, $R^7$=H, $R^8$=H;
(3-k) $R^1$=H, $R^2$=H, $R^6$ is COOPr, $R^7$=H, $R^8$=H;
(3-v) $R^1$=H, $R^2$=H, $R^6$ is COOEt, $R^7$=Me, $R^8$=H;
(3-w) $R^1$=H, $R^2$=H, $R^6$ is COOEt, $R^7$=Me, $R^8$=Br;
(3-x) $R^1$=Me, $R^2$=H, $R^6$ is COOEt, $R^7$=H, $R^8$=H;
(3-y) $R^1$=Me, $R^2$=Me, $R^6$ is COOEt, $R^7$=H, $R^8$=H; or
(3-z) $R^1$=H, $R^2$=H, $R^6$ is COPr, $R^7$=H, $R^8$=H.

In further embodiments, the novel compound is of formula:

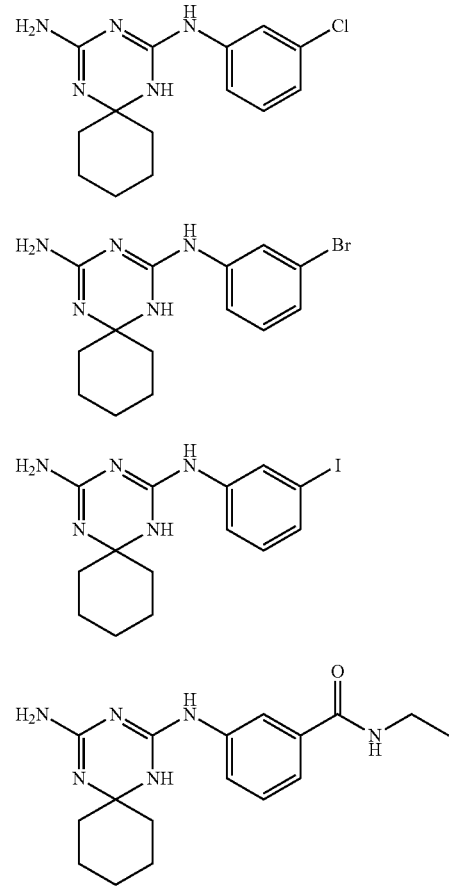

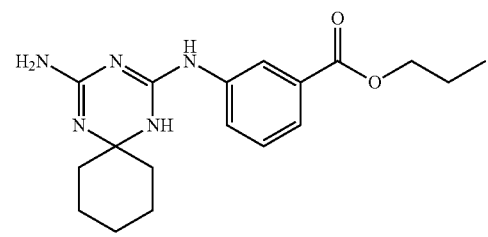

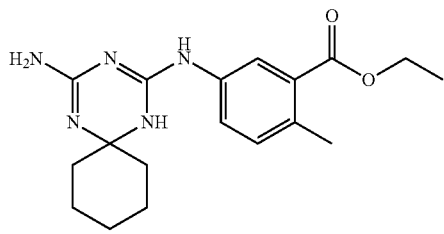

3-v

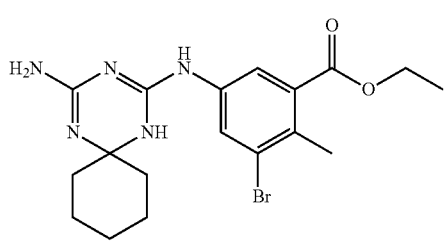

3-w

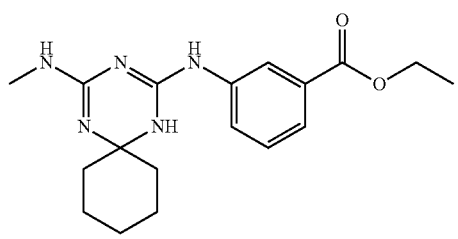

3-x

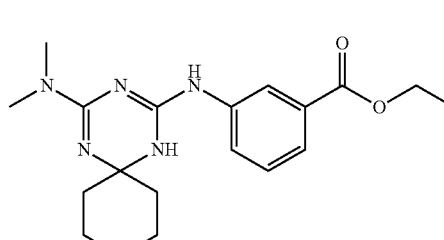

3-y or

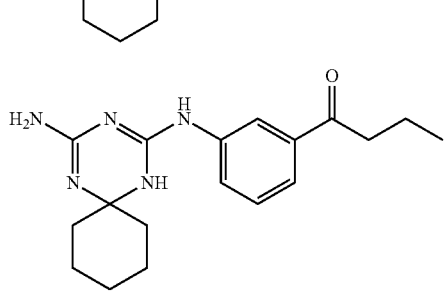

3-z

The invention also provides a pharmaceutical composition comprising a subject compound and a pharmaceutically-acceptable excipient, in unit dosage, particularly therapeutically effective unit dosage, wherein the compound optionally mixed, coformulated or copackaged with a second, different drug indicted for a disorder characterized by over-, or undesirable 5-$HT_{2B}$ receptor signaling, particularly migraine, irritable bowel syndrome (IBS), pulmonary arterial hypertension (PAH), fibrosis, hepatocellular cancer, a small intestinal neuroendocrine tumor, a cardiovascular disorder, or a gastrointestinal (GI) tract disorder.

The invention encompasses all combination of the particular embodiments recited herein.

DESCRIPTION OF PARTICULAR EMBODIMENTS OF THE INVENTION

The following descriptions of particular embodiments and examples are provided by way of illustration and not by way of limitation. Those skilled in the art will readily recognize a variety of noncritical parameters that could be changed or modified to yield essentially similar results.

The invention provides methods and compositions for treating a person having a disorder characterized by over-, or undesirable 5-HT$_{2B}$ receptor signaling, such as migraine, irritable bowel syndrome (IBS), pulmonary arterial hypertension (PAH), fibrosis, including liver fibrosis, lung fibrosis and pulmonary fibrosis; hepatocellular cancer, small intestinal neuroendocrine tumors, cardiovascular disorders, such as chronic heart disease, congestive heart failure and hypertension; and gastrointestinal (GI) tract disorders, especially disorders involving altered motility, hypertonic lower esophageal sphincter and particularly IBS (WO 01/08668, WO 2003035646); disorders of gastric motility, dyspepsia, GERD, tachygastria. Additional documented indications include migraine/neurogenic pain (WO 97/44326); pain (U.S. Pat. No. 5,958,934); anxiety (WO 97/44326); depression (WO 97/44326); benign prostatic hyperplasia (U.S. Pat. No. 5,952,331); sleep disorder (WO 97/44326); panic disorder, obsessive compulsive disorder, alcoholism, hypertension, anorexia nervosa, and priapism (WO 96/24351); incontinence and bladder dysfunction (WO 96/24351); disorders of the uterus, such as hysmenorrhoea, pre-term labour, post-partum remodeling, restenosis, asthma and obstructive airway disease (WO 2003035646).

These indications are all supported by convenient functional, clinical and/or animal activity models, by examples: for migraine (e.g Johnson et al., Cephalalgia, 2003, 23, 117-123), pulmonary hypertension (e.g. Launay et al. 2002, Nat Med 8 (10), 1129-35); IBS (e.g. Borman et al. British J Pharmacol (2002) 135, 1144-51, fibrosis (e.g. Svejda et al. Cancer (Jun. 15, 2010), 2902-12), pulmonary hypertension (e.g. Blanpain et al., Cardiovascular Res 60 (2003) 518-528), liver fibrosis (e.g. Rudell et al. Amer J Pathol, September 2006, 169 (3), 861-76); pulmonary arterial hypertension and ventricular hypertrophy (e.g. Porvasnik et al., 2010, J Pharmacol and Experimental Therapeutics, 334 (2) 364-72), and chronic liver disease (e.g. Ebrahimkhani et al., December 2011, Nature Med 17 (12), 1668-74).

In embodiments, the subject compounds are administered in conjunction with, or mixed, coformulated or copackaged with a second, different drug indicted for a disorder characterized by over-, or undesirable 5-HT$_{2B}$ receptor signaling:

Exemplary Coadministration/Coformulations

| Indication | Second Drug |
|---|---|
| migraine | Pain medications, e.g. NSAID, Ergot alkaloids, triptans |
| irritable bowel syndrome (IBS) | Antidiarrheals, bile acid binding agents |
| pulmonary arterial hypertension (PAH) | Antihypertensives, e.g. calcium channel blockers |
| fibrosis | Immunosuppressants, e.g. corticosteroids |
| hepatocellular cancer | Chemotherapies, e.g. oxorubicin, 5-fluorouracil, cisplatin |
| small intestinal neuroendocrine tumor | Chemotherapies, e.g. cisplatin, etoposide |
| cardiovascular disorder | Antianginals, antiarrythmics, anticoagulants, antihypertensives, beta blockers, calcium channel blockers, cardiac glycosides, diuretics, vasodilators |
| gastrointestinal (GI) tract disorder | Anticholinergics, antidiarreals, antiemetics, antiulcer medications. |

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein. Furthermore, genuses are recited as shorthand for a recitation of all members of the genus; for example, the recitation of (C1-C3) alkyl is shorthand for a recitation of all C1-C3 alkyls: methyl, ethyl and propyl, including isomers thereof.

The term "heteroatom" as used herein generally means any atom other than carbon or hydrogen. Preferred heteroatoms include oxygen (O), phosphorus (P), sulfur (S), nitrogen (N), and halogens, and preferred heteroatom functional groups are haloformyl, hydroxyl, aldehyde, amine, azo, carboxyl, cyanyl, thocyanyl, carbonyl, halo, hydroperoxyl, imine, aldimine, isocyanide, iscyante, nitrate, nitrile, nitrite, nitro, nitroso, phosphate, phosphono, sulfide, sulfonyl, sulfo, and sulfhydryl.

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-C8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-C8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. C2-C8 means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —CH$_2$—CH$_2$—CH$_2$—CH$_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, P, Si and S, wherein the nitrogen, sulfur, and phosphorous atoms may optionally be oxidized and the nitrogen heteroatom may optionally be quaternized. The heteroatom(s) O, N, P and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH3)-CH$_3$. Up to two heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent means a divalent radical derived from heteroalkyl, as exemplified by —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-C8 means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo(C1-C4)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo(C1-C4)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term heteroaryl," refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R''', —OC(O)R', —C(O)R', —CO$_2$R', —CONR'R", —OC(O)NR'R", —NR"C(O)R', —NR'—C(O)NR"R''', —NR'—SO$_2$NR''', —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —CN and —NO$_2$, in a number ranging from zero to three, with those groups having zero, one or two substituents being particularly preferred. R', R" and R''' each independently refer to hydrogen, unsubstituted (C1-C8) alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R"', —OC(O)R', —C(O)R', —CO$_2$R', —CONR'R", —OC(O)NR'R", —NR"C(O)R', —NR"CO$_2$R', —NR'—SO$_2$NR"R"', —S(O)R', —SO2R', —SO$_2$NR'R", —NR"SO$_2$R, —CN and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR"CO$_2$R', —NR'—SO$_2$NR"R"', —SO$_2$R', —SO$_2$NR'R", —NR"SO$_2$R, —CN and —NO$_2$.

Similarly, substituents for the aryl and heteroaryl groups are varied and selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"CO2R', —NR'—C(O)NR"R"', —NR'—SO$_2$NR"R"', —NH—C(NH2)=NH, —NR'C(NH$_2$)=NH, —NH—C(NH$_2$)=NR', —S(O)R', —SO$_2$R', —SO$_2$NR'R", —NR"SO$_2$R, —N$_3$, —CH(Ph)$_2$, perfluoro(C1-C4)alkoxy and perfluoro(C1-C4)alkyl, in a number ranging from zero to the total number of open valences on the aromatic ring system; and where R', R" and R"' are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl. When the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl". Typically, an aryl or heteroaryl group will have from zero to three substituents, with those groups having two or fewer substituents being preferred in the invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —S(O)R', —SO$_2$R', —SO$_2$NR'R", —NR"SO$_2$R, —N$_3$, —CH(Ph)$_2$, perfluoro(C1-C4)alkoxy and perfluoro(C1-C4)alkyl, where R' and R" are as defined above. Further preferred substituents are selected from: halogen, —OR', —OC(O)R', —NR'R", —R', —CN, —NO$_2$, —CO$_2$R', —CONR'R", —NR"C(O)R', —SO$_2$R', —SO$_2$NR'R", —NR"SO$_2$R, perfluoro(C1-C4)alkoxy and perfluoro(C1-C4)alkyl.

The substituent —CO$_2$H, as used herein, includes bioisosteric replacements therefor; see, e.g., The Practice of Medicinal Chemistry; Wermuth, C. G., Ed.; Academic Press: New York, 1996; p. 203.

Two of the substituents on adjacent atoms of the aryl or heteroaryl ring may optionally be replaced with a substituent of the formula -T-C(O)—(CH$_2$)q-U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH2)r-B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)s-X—(CH$_2$)t-, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C1-C6)alkyl.

Preferred substituents are disclosed herein and exemplified in the tables, structures, examples, and claims, and may be applied across different compounds of the invention, i.e. substituents of any given compound may be combinatorially used with other compounds.

In particular embodiments applicable substituents are independently substituted or unsubstituted heteroatom, substituted or unsubstituted, optionally heteroatom C1-C6 alkyl, substituted or unsubstituted, optionally heteroatom C2-C6 alkenyl, substituted or unsubstituted, optionally heteroatom C2-C6 alkynyl, or substituted or unsubstituted, optionally heteroatom C6-C14 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, amine, azo, halogens, carbamoyl, carbonyl, carboxamido, carboxyl, cyanyl, ester, halo, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or triflurom-ethyl ether (OCF3).

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because they may be easier to administer than the parent drug, may be more bioavailable by oral administration than the parent drug, and or may have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Some of the subject compounds possess asymmetric carbon atoms (optical centers) or double bonds; the racemates, diastereomers, geometric isomers and specifically designated or depicted chirality is preferred and in many cases critical for optimal activity; however all such isomers are all intended to be encompassed within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

The term "therapeutically effective amount" refers to the amount of the subject compound that will elicit, to some significant extent, the biological or medical response of a tissue, system, animal or human that is being sought by the researcher, veterinarian, medical doctor or other clinician, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The invention also provides pharmaceutical compositions comprising the subject compounds and a pharmaceutically acceptable excipient, particularly such compositions comprising a unit dosage of the subject compounds, particularly such compositions copackaged with instructions describing use of the composition to treat an applicable disease or condition (herein).

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, lozenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Suitable excipients or carriers and methods for preparing administrable compositions are known or apparent to those skilled in the art and are described in more detail in such publications as *Remington's Pharmaceutical Science*, Mack Publishing Co, NJ (1991). In addition, the compounds may be advantageously used in conjunction with other therapeutic agents as described herein or otherwise known in the art, particularly other anti-necrosis agents. Hence the compositions may be administered separately, jointly, or combined in a single dosage unit.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multipack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The compounds can be administered by a variety of methods including, but not limited to, parenteral, topical, oral, or local administration, such as by aerosol or transdermally, for prophylactic and/or therapeutic treatment. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

The therapeutics of the invention can be administered in a therapeutically effective dosage and amount, in the process of a therapeutically effective protocol for treatment of the patient. For more potent compounds, microgram (ug) amounts per kilogram of patient may be sufficient, for example, in the range of about 1, 10 or 100 ug/kg to about 0.01, 0.1, 1, 10, or 100 mg/kg of patient weight though optimal dosages are compound specific, and generally empirically determined for each compound.

In general, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations. However, the ultimate administration protocol will be regulated according to the judgment of the attending clinician considering such factors as age, condition and size of the patient as well as compounds potency, severity of the disease being treated. For example, a dosage regimen of the compounds can be oral administration of from 10 mg to 2000 mg/day, preferably 10 to 1000 mg/day, more preferably 50 to 600 mg/day, in two to four (preferably two) divided doses. Intermittent therapy (e.g., one week out of three weeks or three out of four weeks) may also be used.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

Examples

We set out to identify new potent 5-HT$_{2B}$ antagonists with novel scaffold and high selectivity via structure-based virtual screening of a large compound database against 5-HT$_{2B}$ crystal structure. First, we refined the binding site conformations to incorporate knowledge of antagonist-bound induced-fit effects and assessed the quality of these models in retrospective virtual screening. We also analyzed the binding site solvent property to derive several interaction patterns as structural filters. Then we adopted a hierarchical strategy integrating different computational methods to screen 5-HT$_{2B}$ antagonists from our in-house compound library. It resulted in 169 candidates meeting the structural and energetic criteria from more than 100,000 diverse drug-like compounds. Among them we identified molecules with an enriched scaffold and which adopt a common binding mode. We validated identified molecules in bioassays. We further improved the binding pose and systematically probed the binding characteristics by testing series of structural modifications. The obtained structure-activity relationship (SAR) results are consistent with our binding model. Our scaffold also exhibits high selectivity over other 5-HT receptors. Our novel scaffold provides 5-HT$_{2B}$ antagonists with improved efficacy and high selectivity.

Synthesis

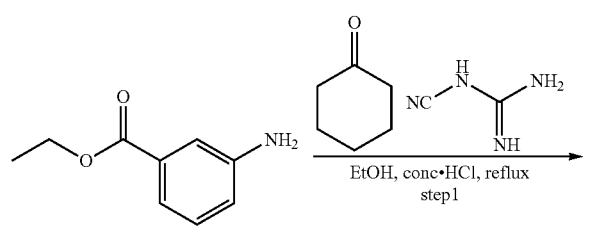

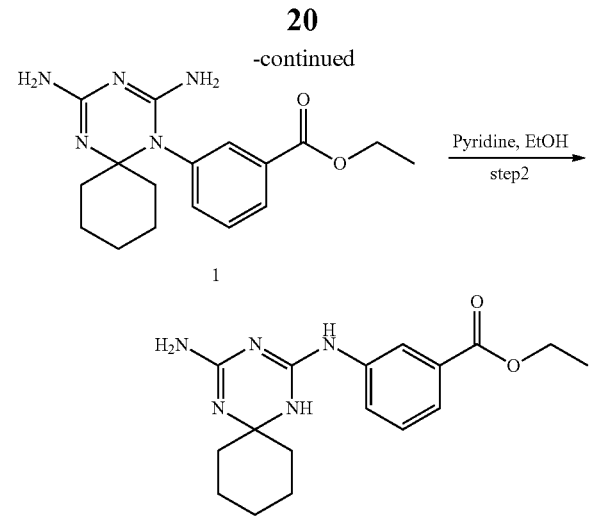

Step 1: Synthesis of ethyl 3-(2,4-diamino-1,3,5-triazaspiro[5.5]undeca-2,4-dien-1-yl)benzoate (1)

A mixture of ethyl 3-aminobenzoate (1.65 g, 10 mmol), cyanoguanidine (925 mg, 11 mmol), conc.HCl (0.83 mL, 10 mmol) and cyclohexanone (981 mg, 10 mmol) in EtOH (1.5 mL) was refluxed. After the completion of the reaction, the solid was filtered to obtain compound 1 (1.2 g, 36%). 1H-NMR (400 MHz, DMSO-d6) δ (ppm) 9.12 (s, 1H), 8.12-8.06 (m, 1H), 7.81 (s, 1H), 7.74-7.56 (m, 4H), 6.43 (s, 1H), 4.45-4.26 (m, 2H), 1.91 (d, J=12.6 Hz, 2H), 1.81-1.43 (m, 5H), 1.43-1.12 (m, 5H), 1.12-0.85 (m, 1H); MS [MH]+ calcd for C17H24N5O2 330.19. found 330.20.

Step 2: Synthesis of ethyl 3-(4-amino-1,3,5-triazaspiro[5.5]undeca-2,4-dien-2-ylamino)benzoate The compound 1 (500 mg, 1.5 mmol) was dissolved in pyridine (2 mL) and EtOH (3 mL), and then the mixture was heated to 120° C. overnight. Then it was concentrated in vacuo to dryness. After water (10 mL) was added, the mixture was stirred at room temperature for 30 min. Then the solid was filtered and dried in vacuo to afford the desired product (220 mg, 44%). 1H-NMR (400 MHz, DMSO-d6) δ (ppm) 10.40 (s, 1H), 9.03 (d, J=7.2 Hz, 2H), 8.02 (d, J=9.1 Hz, 1H), 7.88 (s, 1H), 7.68 (d, J=7.7 Hz, 1H), 7.48 (t, J=7.9 Hz, 1H), 7.27 (s, 1H), 4.33 (q, J=7.1 Hz, 2H), 1.76-1.62 (m, 8H), 1.50-1.27 (m, 5H); MS [MH]+ calcd for C17H24N5O2 330.19. found 330.20.

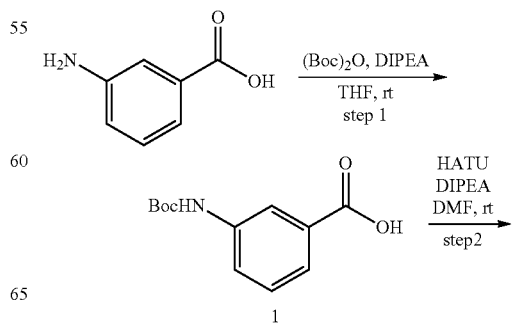

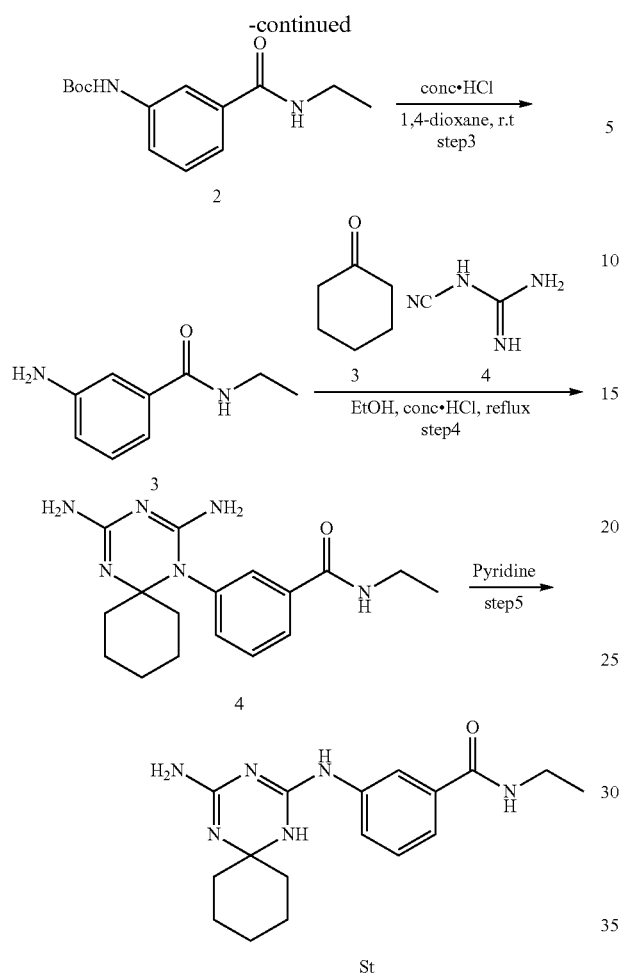

Step 1: Synthesis of 3-(tert-butoxycarbonylamino) benzoic acid (1)

3-aminobenzoic acid (4.4 g, 32.1 mmol) and di-tert-butyl dicarbonate (10.5 g, 48.2 mmol) were dissolved in anhydrous THF (60 mL). Then N-ethyl-N-isopropylpropan-2-amine (8.3 g, 64.2 mmol) was added. The reaction mixture was stirred at room temperature. After the completion of the reaction, it was concentrated in vacco and the residue was extracted with ethyl acetate. The organic layer was concentrated and the residue was purified by column chromatograph to provide the desired product (6.2 g, 82%); MS [MH]− calcd for C12H14NO4 236.10. found 236.10.

Step 2: Synthesis of tert-butyl 3-(ethylcarbamoyl) phenylcarbamate (2)

A mixture of compound 1 (2 g, 8.43 mmol), HATU (6.4 g, 16.9 mmol), N-ethyl-N-isopropylpropan-2-amine (3.27 g, 25.3 mmol) was dissolved in DMF (40 mL), and then the mixture was stirred at room temperature for 30 min. Then ethanamine hydrochloride (2.1 g, 25.3 mmol) was added. After the completion of the reaction, water was added and the organic layer was extracted with EtOAc for three times. The organic layer was concentrated to give the crude product (3.24 g, 100%) which was used in the next step without further purification.

Step 3: Synthesis of 3-amino-N-ethylbenzamide (3)

Compound 2 (3.24 g, 12.3 mmol) was dissolved in dioxane (40 mL), and then conc.HCl (10 mL) was added. The mixture was stirred at room temperature for 8 h. After the completion of the reaction, it was concentrated in vacuo and the residue was purified by column chromatography (silica gel, PE:EA=4:1) to give the desired product (1.4 g, 70%); MS [MH]+ calcd for C9H13N2O 165.09. found 165.10.

Step 4: Synthesis of 3-(2,4-diamino-1,3,5-triazaspiro[5.5]undeca-2,4-dien-1-yl)-N-ethylbenzamide (4)

A mixture of compound 3 (1 g, 6.1 mmol), cyanoguanidine (563 mg, 6.7 mmol), conc.HCl (0.51 mL, 6.1 mmol) and cyclohexanone (599 mg, 6.1 mmol) in EtOH (2 mL) was refluxed. After the completion of the reaction, the solid was filtered to give the desired product (1.18 g, 59%) as a white solid; MS [MH]+ calcd for C17H25N6O 329.20. found 329.20.

Step 5: Synthesis of 3-(4-amino-1,3,5-triazaspiro[5.5]undeca-2,4-dien-2-ylamino)-N-ethylbenzamide The compound of intermediate 4 (300 mg, 0.91 mmol) was dissolved in pyridine (3 mL), the mixture was heated to 120° C. overnight, then it was concentrated in vacuo to give the crude product as a salt. Then the solid was neutralized by sat.NaHCO3 to pH=8. The solid was filtered and dried in vacuo to give the desired product (232 mg, 77%) as a pale pink solid. 1H-NMR (400 MHz, DMSO-d6) δ (ppm) 10.17 (s, 1H), 8.96 (d, J=14.2 Hz, 2H), 8.48 (t, J=5.3 Hz, 1H), 7.78 (d, J=9.3 Hz, 2H), 7.57 (d, J=7.7 Hz, 1H), 7.41 (t, J=7.8 Hz, 1H), 7.18 (s, 1H), 3.32-3.23 (m, 2H), 1.79-1.33 (m, 10H), 1.12 (t, J=7.2 Hz, 3H); MS [MH]+ calcd for C17H25N6O 329.20. found 329.20.

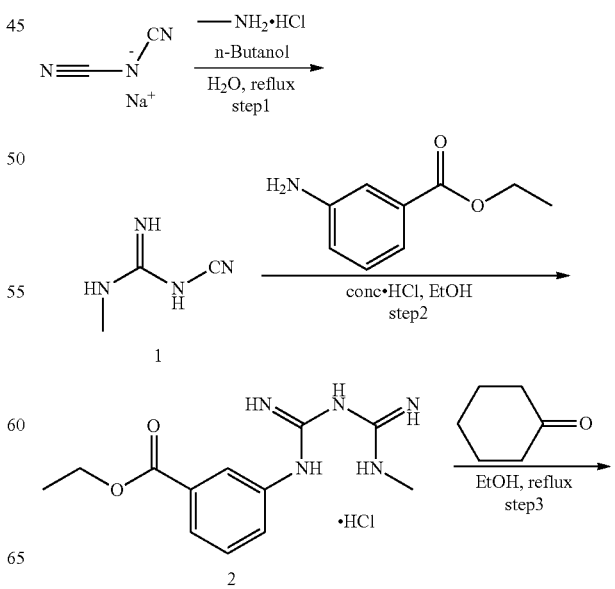

-continued

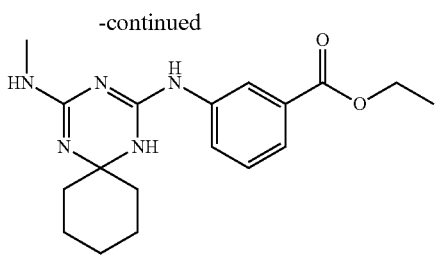

Step 1: Synthesis of 1-cyano-3-methyl-guanidine (1)

Sodium dicyanoamide (5 g, 56.2 mmol) and methylamine hydrochloride (3.8 g, 56.2 mmol) were dissolved in n-butanol (25 mL) and H2O (10 mL). Then the mixture was refluxed. After the completion of the reaction, the mixture was concentrated in vacuo and the residue was purified further by column chromatography (silica gel, DCM:MeOH=10:1) to give the desired product compound 1 (1.7 g, 31%); MS [MH]+ calcd for C3H7N4 99.06. found 99.10.

Step 2: Synthesis of ethyl 3-(3-(N-methylcarbamimidoyl)guanidino)benzoate (2)

A mixture of compound 1 (500 mg, 5.1 mmol), ethyl 3-aminobenzoate (765 mg, 4.63 mmol), conc.HCl (0.39 mL, 4.63 mmol) in EtOH (2 mL) was refluxed for 6 h. Then the desired product compound 2 was obtained by filtration (510 mg, 37%); MS [MH]+ calcd for C12H18N5O2 264.14. found 264.14.

Step 3: Synthesis of ethyl 3-(4-(methylamino)-1,3,5-triazaspiro[5.5]undeca-2,4-dien-2-ylamino)benzoate Compound of intermediate 2 (510 mg, 1.7 mmol) in cyclohexanone (15 mL) and EtOH (5 mL) was refluxed overnight. Then it was cooled to room temperature. Sat. aq. NaHCO3 (25 mL) was added. The mixture was extracted by DCM (50 mL*3) and washed by brine (30 mL*1). The organic layers were combined and concentrated in vacuo to afford a crude product, which was purified by column chromatography (silica gel, DCM:MeOH=30:1 to 20:1) to provide the desired product compound 3 (230 mg, 39%). 1H-NMR (400 MHz, DMSO-d6) δ (ppm) 8.90 (s, 1H), 7.97 (s, 1H), 7.76 (d, J=7.9 Hz, 1H), 7.34 (d, J=7.6 Hz, 1H), 7.23 (t, J=7.8 Hz, 1H), 6.42 (s, 1H), 5.77 (s, 1H), 4.27 (q, J=7.1 Hz, 2H), 2.73 (d, J=4.2 Hz, 3H), 1.81-1.26 (m, 12H); MS [MH]+ calcd for C18H26N5O2 344.20. found 344.20.

Antagonist Activity Assay

Stable cell line, CHO-K1/5-HT$_{2B}$, was applied for the cellular screening of the compound exhibited significant activities in 5-HT$_{2B}$ antagonist assay using FLIPR method. Briefly, CHO-K1 cells expressing 5-HT$_{2B}$ were seeded in a 384-well black-wall, clear-bottom plate at a density of 20,000 cells per well in 20 μL of growth medium (10% dialyzed FBS+90% F12), 18 hours prior to the day of experiment and maintained at 37° C./5% CO2. 20 μL of dye-loading solution and 10 μL of tested compound solution (at concentrations five times to the final assay concentrations) were added into the well. Then the plate was placed into a 37° C. incubator for 60 minutes, followed by 15 minutes at room temperature. At last, 12.5 μL of control agonist (at concentrations five times to the EC$_{80}$ concentrations) was added. The control agonist was added to reading plate at 20 s and the fluorescence signal was monitored for an additional 100 s (21 s to 120 s). In screening, cells stimulated with assay buffer (HBSS-HEPES) containing 0.1% DMSO were chosen as background; cell stimulated with 12 nM (EC$_{80}$ of the cell line) of 5-HT were chosen as the agonist control; cell treated with SB206553 were chosen as positive control of the screening.

Data acquisition and analyses are performed using ScreenWorks (version 3.1) program. The average fluorescent intensity value during 1 s to 20 s calculated as the baseline reading. The relative fluorescent units (ΔRFU) intensity values were calculated with the maximal fluorescent units (21 s to 120 s) subtracting the average value of baseline reading. The % inhibition of the test article is calculated from the following equation:

$$\% \text{ inhibition} = [1-(\Delta RFU_{Compound}-\Delta RFU_{Background})/(\Delta RFU_{Agonist\ control}-\Delta RFU_{Background})]*100$$

| Antagonist Activity Tested on 5-HT2B Receptors | | | |
|---|---|---|---|
| No. | Structure | % Inhibition at 1 μM | IC$_{50}$ (nM) |
| 1-a | 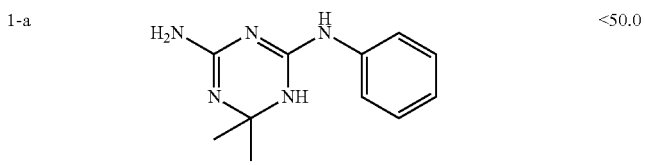 | <50.0 | |
| 1-b | 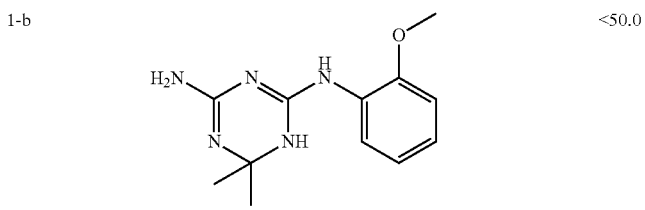 | <50.0 | |

-continued

| Antagonist Activity Tested on 5-HT2B Receptors | | | |
|---|---|---|---|
| No. | Structure | % Inhibition at 1 μM | IC$_{50}$ (nM) |
| 1-c | | 75.9 ± 11.5 | 327.6 |
| 1-d | | 93.1 ± 4.2 | 1636 |
| 1-e | | <50.0 | |
| 1-f | | <50.0 | 2508 |
| 1-g | | <50.0 | |
| 1-h | | <50.0 | |
| 1-i | | <50.0 | |
| 2-a | | 63.4 ± 15.1 | 1056 |

-continued
| No. | Structure | % Inhibition at 1 μM  IC$_{50}$ (nM) |
|---|---|---|
| | Antagonist Activity Tested on 5-HT2B Receptors | |
| 2-b | 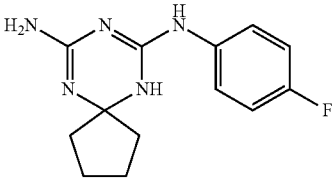 | <50.0 |
| 2-c | 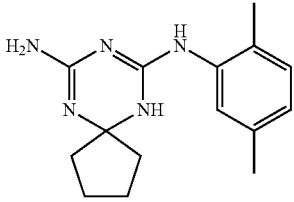 | <50.0 |
| 2-d | 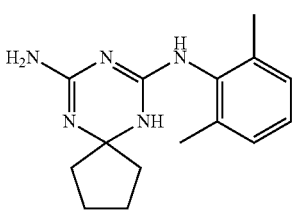 | <50.0 |
| 3-a | 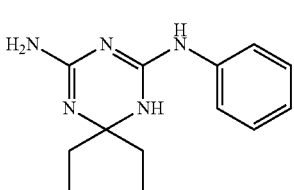 | <50.0 |
| 3-b | 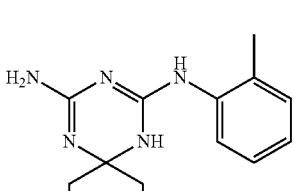 | <50.0 |
| 3-c | 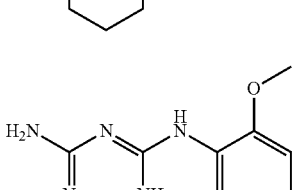 | <50.0 |
| 3-d | 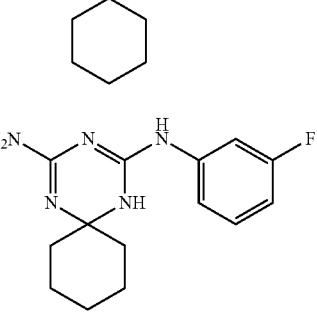 | 90.9 ± 2.9 |

-continued
| Antagonist Activity Tested on 5-HT2B Receptors | | | |
|---|---|---|---|
| No. | Structure | % Inhibition at 1 μM | IC$_{50}$ (nM) |
| 3-e1 | 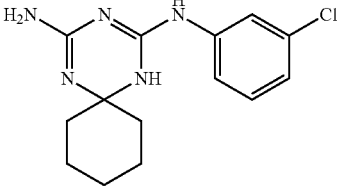 | 95.5 (est) | |
| 3-e2 | 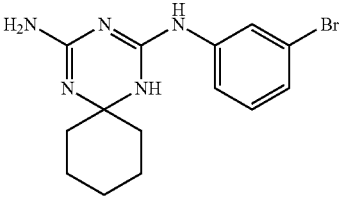 | 97.4 ± 2.2 | 33.35 |
| 3-f | 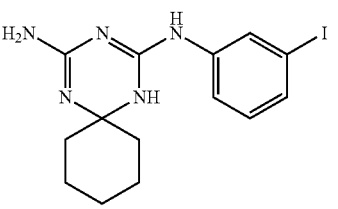 | 101.8 ± 4.5 | |
| 3-g | 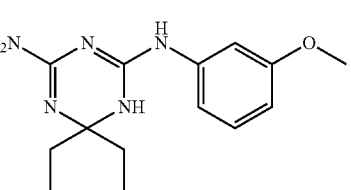 | 84.6 ± 1.2 | 280.0 |
| 3-h | 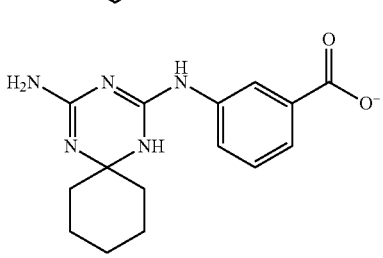 | <50.0 | |
| 3-i | 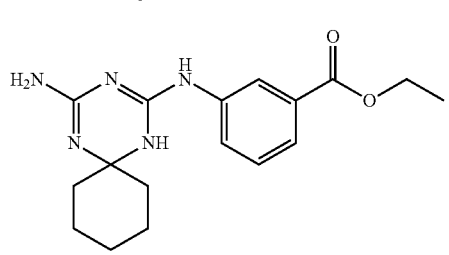 | 107.2 ± 0.6 | 27.30 |
| 3-j | 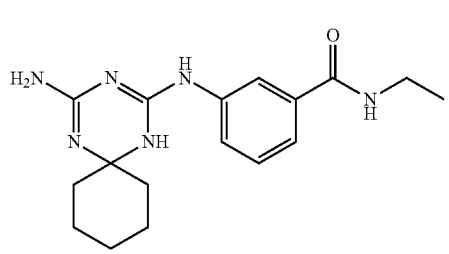 [SMILES: CCNC(=O)c1cccc(NC2=NC(N)=NC3(CCCCC3)N2)c1] | 95.5 ± 4.8 | 104.0 |

-continued

| Antagonist Activity Tested on 5-HT2B Receptors ||||
| No. | Structure | % Inhibition at 1 μM | IC$_{50}$ (nM) |
| --- | --- | --- | --- |
| 3-k | 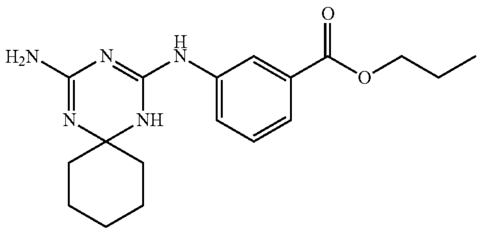 [SMILES: CCCOC(=O)c1cccc(NC2=NC(N)=NC3(CCCCC3)N2)c1] | 110.5 ± 2.7 | 18.10 |
| 3-l | 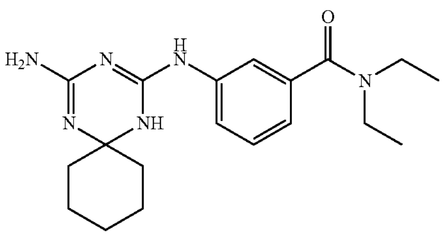 [SMILES: CCN(CC)C(=O)c1cccc(NC2=NC(N)=NC3(CCCCC3)N2)c1] | <50.0 | |
| 3-m | 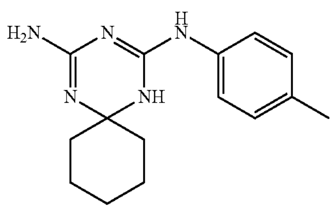 [SMILES: Cc1ccc(NC2=NC(N)=NC3(CCCCC3)N2)cc1] | 50.2 ± 8.0 | 485.9 |
| 3-n | 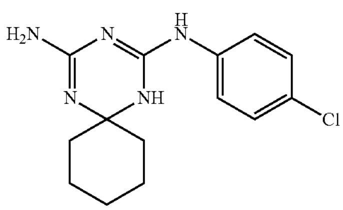 [SMILES: NC1=NC2(CCCCC2)NC(Nc2ccc(Cl)cc2)=N1] | 57.2 ± 5.4 | 531.0 |
| 3-o | 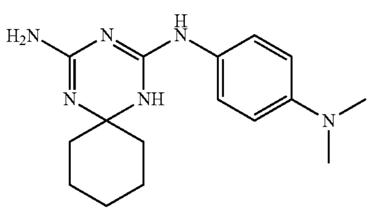 [SMILES: CN(C)c1ccc(NC2=NC(N)=NC3(CCCCC3)N2)cc1] | <50.0 | |
| 3-p | 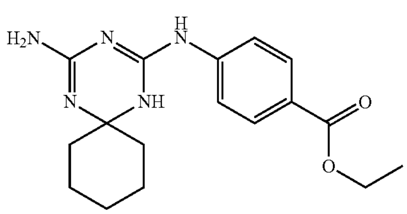 [SMILES: CCOC(=O)c1ccc(NC2=NC(N)=NC3(CCCCC3)N2)cc1] | 108.6 ± 04.2 | |
| 3-q | 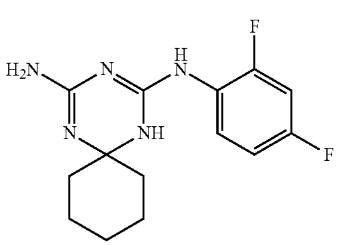 [SMILES: NC1=NC2(CCCCC2)NC(Nc2ccc(F)cc2F)=N1] | <50.0 | |

-continued
| | Antagonist Activity Tested on 5-HT2B Receptors | | |
|---|---|---|---|
| No. | Structure | % Inhibition at 1 μM | $IC_{50}$ (nM) |
| 3-r | 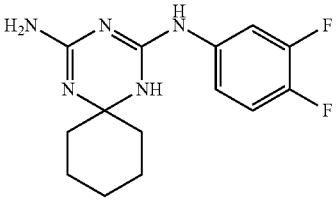 [SMILES: NC1=NC2(CCCCC2)NC(Nc2ccc(F)c(F)c2)=N1] | 66.5 ± 2.1 | |
| 3-s | 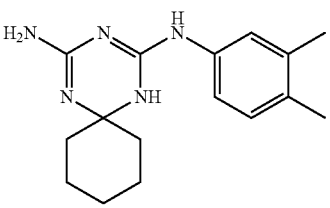 | 95.7 ± 1.9 | 177.0 |
| 3-t | 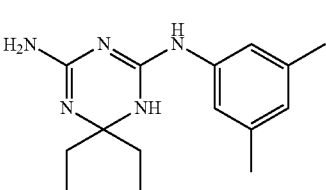 | 69.1 ± 2.7 | 476.0 |
| 3-u | 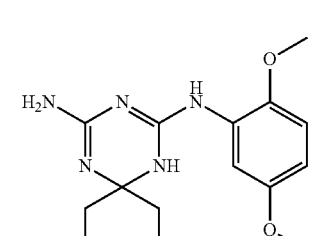 | 81.1 ± 6.7 | 622.4 |
| 3-v | 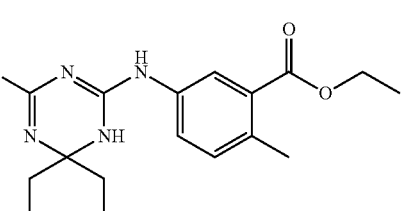 | 107.5 ± 1.5 | |
| 3-w | 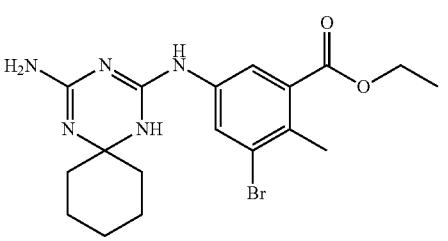 [SMILES: CCOC(=O)c1cc(NC2=NC(N)=NC3(CCCCC3)N2)cc(Br)c1C] | 92.8 ± 3.1 | |

Antagonist Activity Tested on 5-HT2B Receptors

| No. | Structure | % Inhibition at 1 µM | IC$_{50}$ (nM) |
|---|---|---|---|
| 3-x | 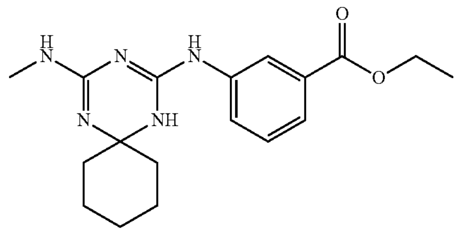 [SMILES: CCOC(=O)c1cccc(NC2=NC(NC)=NC3(CCCCC3)N2)c1] | 107.8 ± 0.0 | 49.39 |
| 3-y | 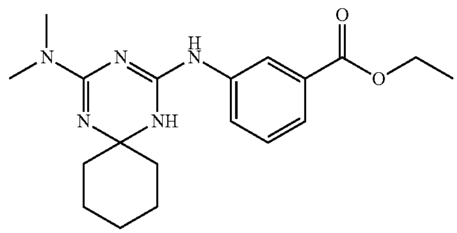 [SMILES: CCOC(=O)c1cccc(NC2=NC(N(C)C)=NC3(CCCCC3)N2)c1] | 91.8 ± 0.4 | 284.5 |
| 3-z | 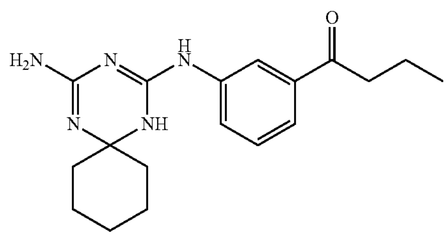 [SMILES: CCCC(=O)c1cccc(NC2=NC(N)=NC3(CCCCC3)N2)c1] | 106.0 ± 0.8 | 35.83 |

REFERENCES

1. Overington J P, Al-Lazikani B, Hopkins A L. How many drug targets are there? Nat Rev Drug Discov 2006; 5(12):993-996.
2. Kolb P, Rosenbaum D M, Irwin J J, Fung J J, Kobilka B K, Shoichet B K. Structure-based discovery of beta2-adrenergic receptor ligands. Proc Natl Acad Sci USA 2009; 106(16):6843-6848.
3. Carlsson J, Yoo L, Gao Z G, Irwin J J, Shoichet B K, Jacobson K A. Structure-based discovery of A2A adenosine receptor ligands. J Med Chem 2010; 53(9):3748-3755.
4. Carlsson J, Coleman R G, Setola V, Irwin J J, Fan H, Schlessinger A, Sali A, Roth B L, Shoichet B K. Ligand discovery from a dopamine D3 receptor homology model and crystal structure. Nat Chem Biol 2011; 7(11):769-778.
5. Wacker D, Wang C, Katritch V, Han G W, Huang X P, Vardy E, McCorvy J D, Jiang Y, Chu M, Siu F Y, Liu W, Xu H E, Cherezov V, Roth B L, Stevens R C. Structural features for functional selectivity at serotonin receptors. Science 2013; 340(6132):615-619.
6. Liu W, Wacker D, Gati C, Han G W, James D, Wang D, Nelson G, Weierstall U, Katritch V, Barty A, Zatsepin N A, Li D, Messerschmidt M, Boutet S, Williams G J, Koglin J E, Seibert M M, Wang C, Shah S T, Basu S, Fromme R, Kupitz C, Rendek K N, Grotjohann I, Fromme P, Kirian R A, Beyerlein K R, White T A, Chapman H N, Caffrey M, Spence J C, Stevens R C, Cherezov V. Serial femtosecond crystallography of G protein-coupled receptors. Science 2013; 342(6165):1521-1524.
7. Rothman R B, Baumann M H, Savage J E, Rauser L, McBride A, Hufeisen S J, Roth B L. Evidence for possible involvement of 5-HT(2B) receptors in the cardiac valvulopathy associated with fenfluramine and other serotonergic medications. Circulation 2000; 102(23):2836-2841.
8. Hutcheson J D, Setola V, Roth B L, Merryman W D. Serotonin receptors and heart valve disease—it was meant 2B. Pharmacol Ther 2011; 132(2):146-157.
9. Brea J, Castro-Palomino J, Yeste S, Cubero E, Parraga A, Dominguez E, Loza M I. Emerging opportunities and concerns for drug discovery at serotonin 5-HT2B receptors. Curr Top Med Chem 2010; 10(5):493-503.
10. Panconesi A, Sicuteri R. Headache induced by serotonergic agonists—a key to the interpretation of migraine pathogenesis? Cephalalgia 1997; 17(1):3-14.
11. Borman R A, Tilford N S, Harmer D W, Day N, Ellis E S, Sheldrick R L, Carey J, Coleman R A, Baxter G S. 5-HT(2B) receptors play a key role in mediating the excitatory effects of 5-HT in human colon in vitro. Br J Pharmacol 2002; 135(5):1144-1151.
12. Spiller R. Serotonergic agents and the irritable bowel syndrome: what goes wrong? Curr Opin Pharmacol 2008; 8(6):709-714.
13. Launay J M, Herve P, Peoc'h K, Tournois C, Callebert J, Nebigil C G, Etienne N, Drouet L, Humbert M, Simonneau G, Maroteaux L. Function of the serotonin 5-hydroxytryptamine 2B receptor in pulmonary hypertension. Nat Med 2002; 8(10):1129-1135.
14. Porvasnik S L, Germain S, Embury J, Gannon K S, Jacques V, Murray J, Byrne B J, Shacham S, Al-Mously F. PRX-08066, a novel 5-hydroxytryptamine receptor 2B antagonist, reduces monocrotaline-induced pulmonary arterial hypertension and right ventricular hypertrophy in rats. J Pharmacol Exp Ther 2010; 334(2):364-372.
15. Ebrahimkhani M R, Oakley F, Murphy L B, Mann J, Moles A, Perugorria M J, Ellis E, Lakey A F, Burt A D, Douglass A, Wright M C, White S A, Jaffre F, Maroteaux L, Mann D A. Stimulating healthy tissue regeneration by targeting the 5-HT(2)B receptor in chronic liver disease. Nat Med 2011; 17(12):1668-1673.
16. Soll C, Jang J H, Riener M O, Moritz W, Wild P J, Graf R, Clavien P A. Serotonin promotes tumor growth in human hepatocellular cancer. Hepatology 2010; 51(4):1244-1254.
17. Soll C, Riener M O, Oberkofler C E, Hellerbrand C, Wild P J, DeOliveira M L, Clavien P A. Expression of serotonin receptors in human hepatocellular cancer. Clin Cancer Res 2012; 18(21):5902-5910.
18. Lin X, Huang X P, Chen G, Whaley R, Peng S, Wang Y, Zhang G, Wang S X, Wang S, Roth B L, Huang N. Life beyond kinases: structure-based discovery of sorafenib as nanomolar antagonist of 5-HT receptors. J Med Chem 2012; 55(12):5749-5759.
19. Poissonnet G, Parmentier J G, Boutin J A, Goldstein S. The emergence of selective 5-HT 2B antagonists structures, activities and potential therapeutic applications. Mini Rev Med Chem 2004; 4(3):325-330.

What is claimed is:

1. A method for treating a person in need thereof having a disorder characterized by undesirable 5-HT$_{2B}$ receptor signaling, comprising administering to the person a 5-HT$_{2B}$ antagonist of formula I:

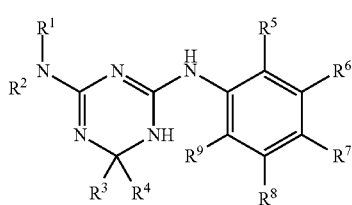

(I)

wherein:
$R^1$ and $R^2$ are independently H or methyl;
$R^3$ and $R^4$ are independently a C1-C4 alkyl, or $R^3$ and $R^4$ are joined to form a C3-C8 cycloalkyl; and
$R^5$-$R^9$ are independently H, halogen, hydroxyl, or an optionally substituted C1-C4 alkyl, C1-C4 alkyoxy, carbonyl, carboxyl, or amine;
or salt thereof,
wherein the disorder is migraine, pulmonary arterial hypertension (PAH), fibrosis, or a gastrointestinal (GI) tract disorder selected from the group consisting of hypertonic lower esophageal sphincter, irritable bowel syndrome (IBS), gastric motility disorder, dyspepsia, gastroesophageal reflux disease (GERD), and tachygastria.

2. The method of claim 1 wherein:
$R^1$ and $R^2$ are independently H or methyl;
$R^3$ and $R^4$ are independently C1-C3 alkyl, or $R^3$ and $R^4$ are joined to form C4-C7 cycloalkyl;
$R^5$ and $R^9$ are independently H, halogen, methyl or methoxyl; and
$R^6$-$R^8$ are independently H, halogen, methyl, —OR$^{10}$, COR$^{10}$, COOR$^{10}$, or CONR$^{10}$R$^{10}$, wherein each R$^{10}$ is independently H or C1-C4 alkyl.

3. The method of claim 1 wherein:
$R^1$ and $R^2$ are independently H or methyl;
$R^3$ and $R^4$ are methyl or $R^3$ and $R^4$ form cyclopentyl or cyclohexyl;
$R^5$ is H, halogen, methyl or methoxyl;
$R^6$ is H, halogen (F, Cl, Br, I), methyl, methoxyl, or —OR$^{10}$, COR$^{10}$, COOR$^{10}$, or CONR$^{10}$R$^{10}$, wherein each R$^{10}$ is independently H or C1-C4 alkyl;
$R^7$ is H, halogen, methyl, —OR$^{10}$ or COOR$^{10}$, wherein each R$^{10}$ is independently H or C1-C3 alkyl;
$R^8$ is H, halogen, methyl or methoxyl; and
$R^9$ is H or methyl.

4. The method of claim 1 wherein the antagonist is of formula:

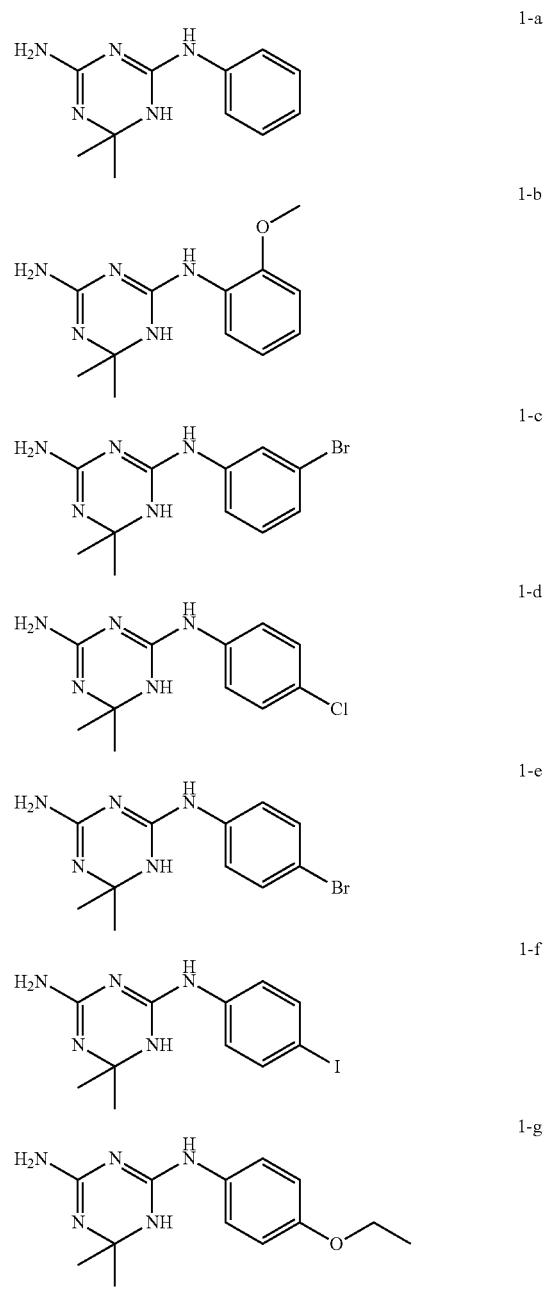

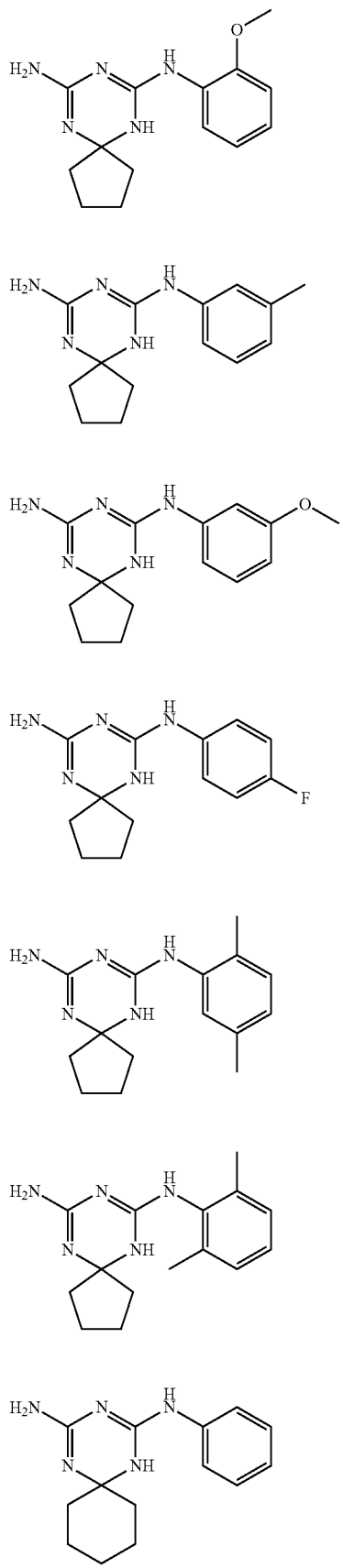
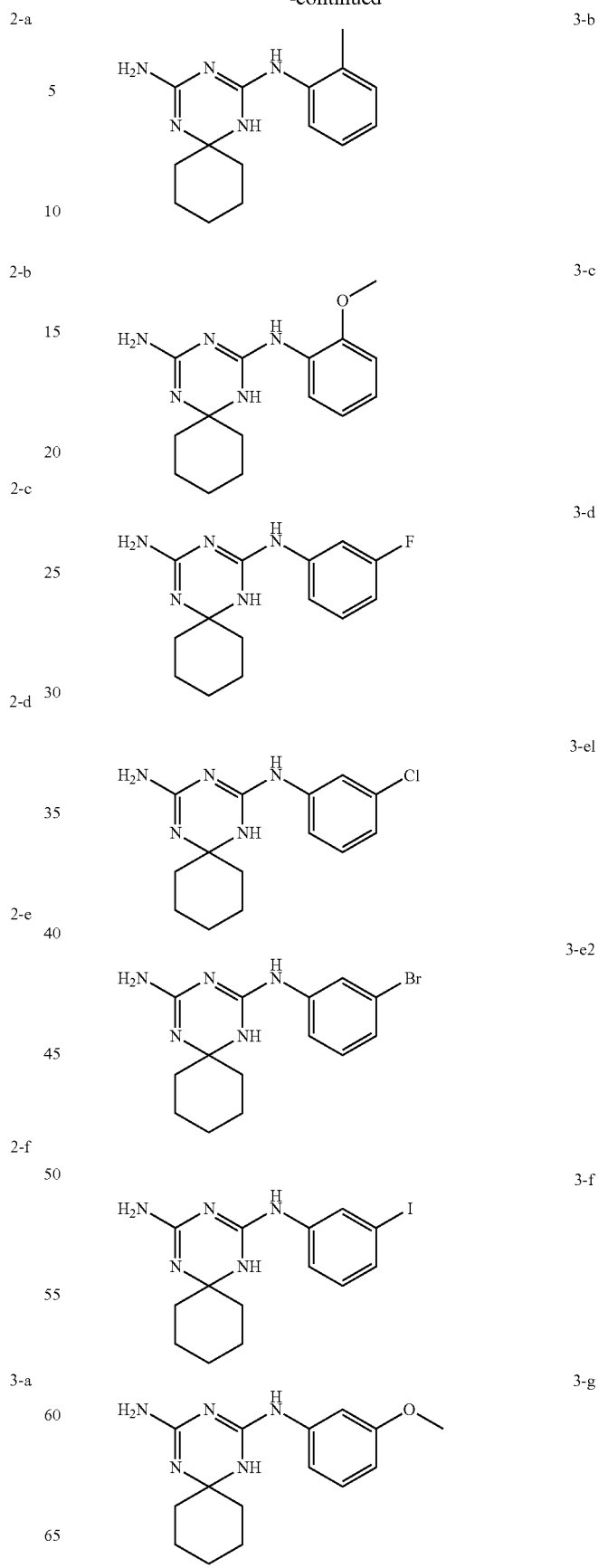

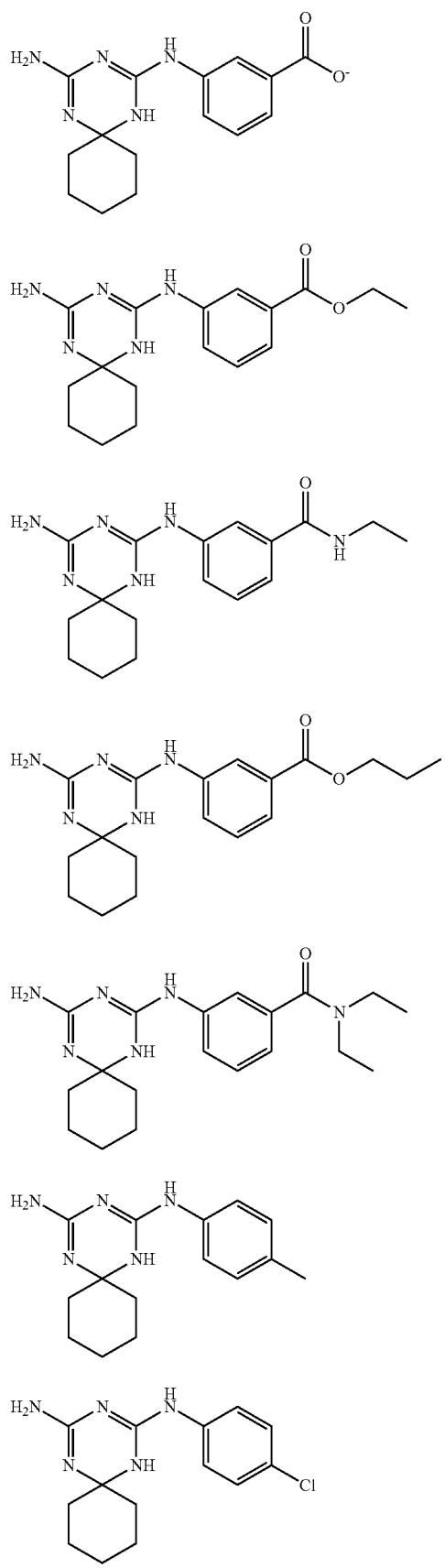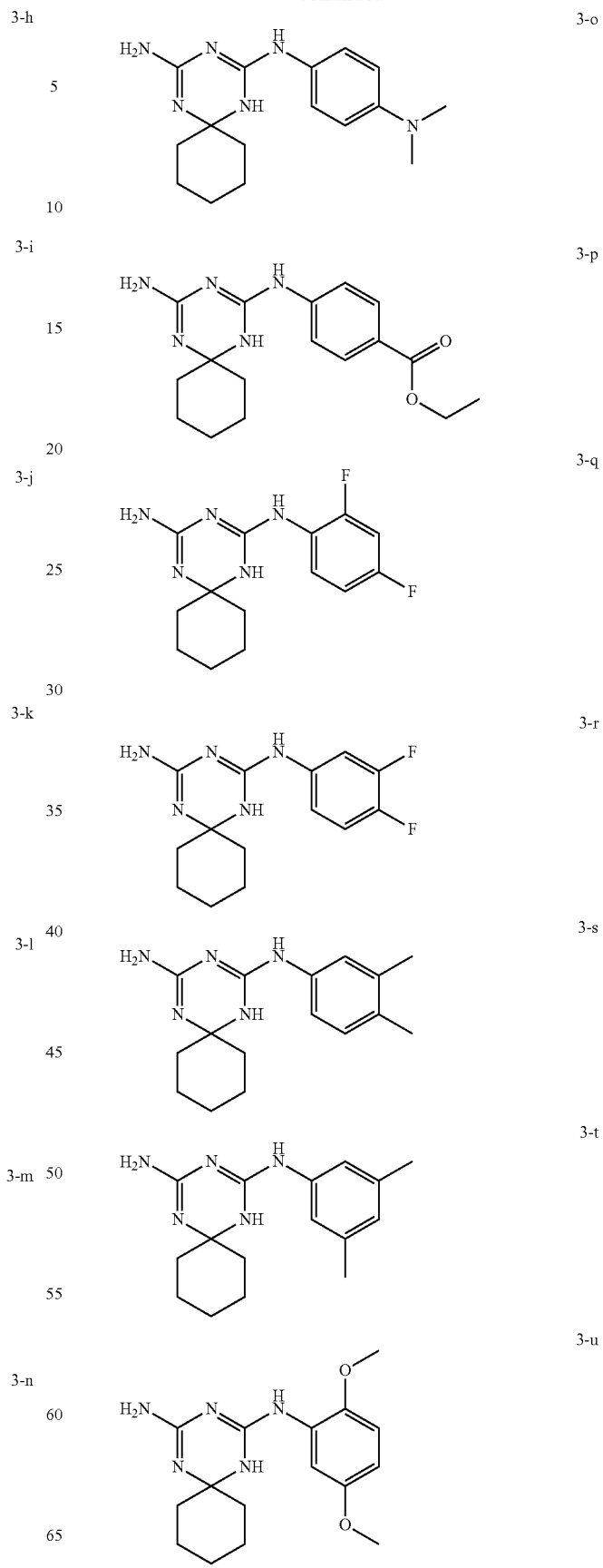

5. The method of claim 1 wherein:

$R^1$ and $R^2$ are independently H or Me;

$R^3$ and $R^4$ form cyclohexyl;

$R^5$ is H;

$R^6$ is $COR^{10}$, $COOR^{10}$, or $CONR^{10}R^{10}$, wherein each $R^{10}$ is independently H or C1-C4 alkyl;

$R^7$ is H or methyl;

$R^8$ is H or halogen; and $R^9$ is H;

or salt thereof.

6. The method of claim 1 wherein the antagonist is of formula:

-continued

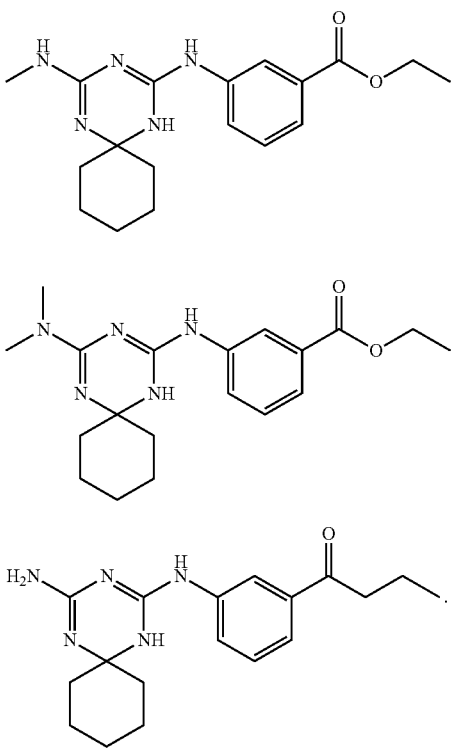

3-x 3-y 3-z

7. The method of claim 1 wherein the antagonist is of formula:

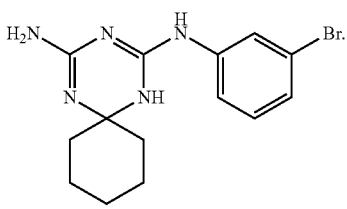

8. The method of claim 1 further comprising the step of detecting a resultant amelioration of the disorder.

9. The method of claim 1 further comprising the antecedent step of diagnosing the disorder.

10. The method of claim 1 further comprising administering to the person a second, different drug indicted for the disorder.

11. The method of claim 1 further comprising administering to the person a second, different drug indicted for the disorder, wherein the second drug and disorder are selected from the following combinations:

| INDICATION | SECOND DRUG |
| --- | --- |
| migraine | pain medications |
| irritable bowel syndrome (IBS) | antidiarrheals, bile acid binding agents |
| pulmonary arterial hypertension (PAH) | antihypertensives |
| fibrosis | immunosuppressants |
| hepatocellular cancer | chemotherapies |
| small intestinal neuroendocrine tumor | chemotherapies |
| cardiovascular disorder | antianginals, antiarrythmics, anticoagulants, antihypertensives, beta blockers, calcium channel blockers, cardiac glycosides, diuretics, vasodilators |
| gastrointestinal (GI) tract disorder | anticholinergics, antidiarreals, antiemetics, antiulcer medications. |

12. The method of claim 1 wherein the disorder is migraine.

13. The method of claim 1 wherein the disorder is irritable bowel syndrome (IBS).

14. The method of claim 1 wherein the disorder is pulmonary arterial hypertension (PAH).

15. The method of claim 1 wherein the disorder is fibrosis.

16. The method of claim 1 wherein the disorder is dyspepsia.

17. The method of claim 1 wherein the disorder is gastroesophageal reflux disease (GERD).

18. The method of claim 7 wherein the disorder is irritable bowel syndrome (IBS).

19. The method of claim 7 wherein the disorder is pulmonary arterial hypertension (PAH).

20. The method of claim 7 wherein the disorder is fibrosis.

* * * * *